(12) United States Patent
Alluri

(10) Patent No.: US 6,524,967 B1
(45) Date of Patent: Feb. 25, 2003

(54) METHOD FOR INCORPORATING NITROGEN INTO A DIELECTRIC LAYER USING A SPECIAL PRECURSOR

(75) Inventor: Prasad V. Alluri, Round Rock, TX (US)

(73) Assignee: Motorola, Inc., Schaumburg, IL (US)

(*) Notice: Subject to any disclaimer, the term of this patent is extended or adjusted under 35 U.S.C. 154(b) by 150 days.

(21) Appl. No.: 09/630,083

(22) Filed: Aug. 1, 2000

(51) Int. Cl.$^7$ ............................................. H01L 21/469
(52) U.S. Cl. ........................ 438/758; 438/778; 438/783; 438/787; 438/791
(58) Field of Search ................................. 438/758, 761, 438/762, 765, 778, 584, 597, 618, 783, 784, 787, 791, FOR 154, 591, 287, 240, 785; 257/410, 411, 296; 427/99, 124, 126.3, 126.4

(56) References Cited

U.S. PATENT DOCUMENTS

| | | | |
|---|---|---|---|
| 3,480,653 A | | 11/1969 | Pande et al. |
| 5,227,334 A | * | 7/1993 | Sandhu |
| 5,820,664 A | * | 10/1998 | Gardiner et al. |
| 6,063,443 A | | 5/2000 | Uchikawa et al. |

FOREIGN PATENT DOCUMENTS

| | | |
|---|---|---|
| JP | 2000-58526 | 2/2000 |
| WO | WO99/02756 | 1/1999 |

OTHER PUBLICATIONS

Bohra et al, "Organic Compounds of Vth Group Elements: Part II—Reaction of Niobium Pantaethoxide with Oximes & Diethylhydroxylamine," Indian Journal of Chemistry, vol. 12, Aug. 1974, pp. 855–857.

Mehrotra et al., "Reactions of Tantalum Penta–Ethoxide and Oximes and Diethyl–hydroxylamine," A. anorg. Allg. Chem. 899, 338–344 (1973).

Singh et al., "Reactions of Oximes and Diethylhydroxylamine with Titanium Alkoxides," J. Chem. Soc., (A), 1971, pp. 2440–2444.

* cited by examiner

*Primary Examiner*—Olik Chaudhuri
*Assistant Examiner*—Thanh Pham
(74) *Attorney, Agent, or Firm*—Robert A. Rodriguez

(57) ABSTRACT

A metal-organic precursor suitable for use in a chemical vapor deposition formation of dielectric layer is disclosed. The precursor comprises a moiety that includes a first metal atom, an oxygen atom, and a nitrogen atom. The oxygen atom is chemically bonded to the metal atom and to the nitrogen atom. The first metal atom may be a Group III, Group IV, or Group V transition metals such as yttrium, lanthanum, titanium, zirconium, hafnium, niobium, and tantalum or another metal such as aluminum. The precursor may include one or more alkoxy groups bonded to the first metal atom. The precursor may be characterized as a $M(OCR_3)_{X-Y-Z}(ONR_2)_Y(OSiR_3)_Z$ molecule where Y is an integer from 1 to (X-1), Z is an integer from 0 to X-1, X is an integer from 3 to 5 depending upon the valency of M and (Y+Z) is less than or equal to X. In one embodiment the precursor further includes one or more siloxy or alkyl siloxy groups bonded to the first metal atom. The precursor is suitable for chemical vapor deposition process used to deposit a dielectric layer on a semiconductor substrate. In this embodiment, the dielectric layer may be intended as a gate dielectric layer or a capacitor dielectric layer.

5 Claims, 2 Drawing Sheets

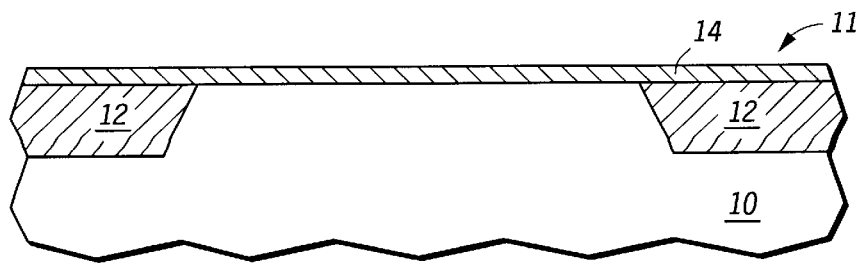
FIG.1
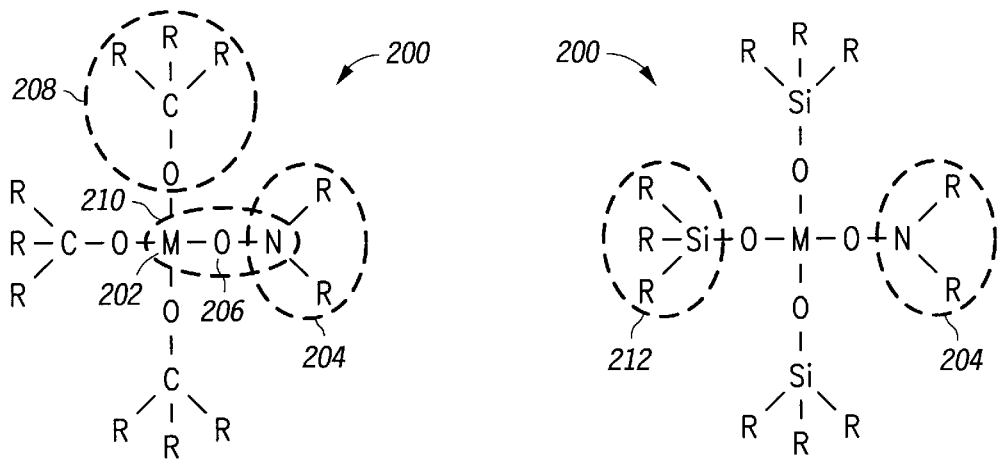
FIG.2                                   FIG.3
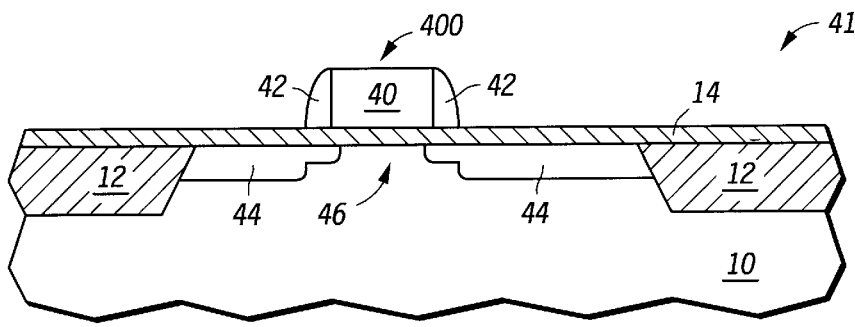
FIG.4
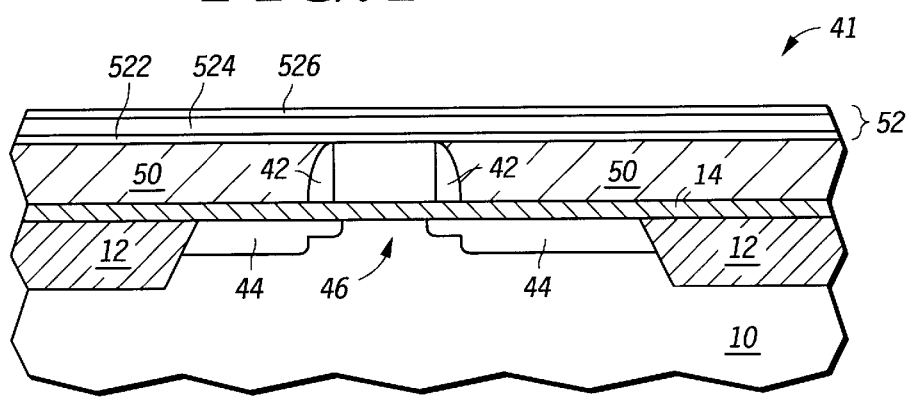
FIG.5

METHOD FOR INCORPORATING NITROGEN INTO A DIELECTRIC LAYER USING A SPECIAL PRECURSOR

FIELD OF THE INVENTION

The invention is related to the field of semiconductor fabrication and more particularly to a method for incorporating nitrogen into a dielectric layer.

BACKGROUND OF THE INVENTION

In the field of semiconductor fabrication, boron penetration from p-type polysilicon into the transistor channel region is a well-known problem in CMOS processes. The presence of boron in the transistor channel can act as a counter dopant in a PMOS transistor, thereby undesirably altering the threshold voltage of the P-channel transistors. Manufacturers have addressed this boron penetration problem in a variety of methods including introducing nitrogen into the transistor gate dielectric. The presence of nitrogen in the gate dielectric is believed to significantly retard the ability of impurities such as boron to migrate. Nitrogen has been introduced into the bulk of the dielectric layer itself and at the interface between the dielectric and the underlying silicon substrate. Introducing nitrogen at the silicon-dielectric interface is known to increase the interface state density (Dit) thereby causing degradation in device performance. Thus, it is preferable to introduce nitrogen into the bulk of the dielectric itself. Introducing nitrogen into the dielectric bulk, however, is difficult to implement in processes using high-K dielectric layers such as metal oxides. The use of a remote nitrogen plasma has been proposed to facilitate the introduction of nitrogen into the dielectric layer with a chemical vapor deposition (CVD) process. Typically, multiple precursors are required to implement this CVD process. In addition to introducing process complexities, multiple precursor processes require a highly reactive process to form the necessary metal-oxygen nitrogen bond. To achieve sufficient reactivity, it is typically necessary although undesirable to increase the deposition temperature or power (in the case of a plasma process). In addition, it is generally more difficult to maintain control of a multiple precursor process in a manufacturing environment. Therefore, it would be desirable to implement a process for forming a nitrogen bearing high-K dielectric using a single precursor that contains a metal-oxygen-nitrogen moiety.

BRIEF DESCRIPTION OF THE DRAWINGS

FIG. 1 is a partial cross-sectional view of a semiconductor substrate on which a dielectric layer has been formed;

FIG. 2 is a representation of a molecule suitable for use in one embodiment of the present invention;

FIG. 3 is a representation of an alternative molecule suitable for use in the present invention;

FIG. 4 is a partial cross-sectional view of a semiconductor substrate subsequent to the processing step shown in FIG. 1;

FIG. 5 is a processing step subsequent to FIG. 4;

DETAILED DESCRIPTION OF THE DRAWINGS

Figure 6:
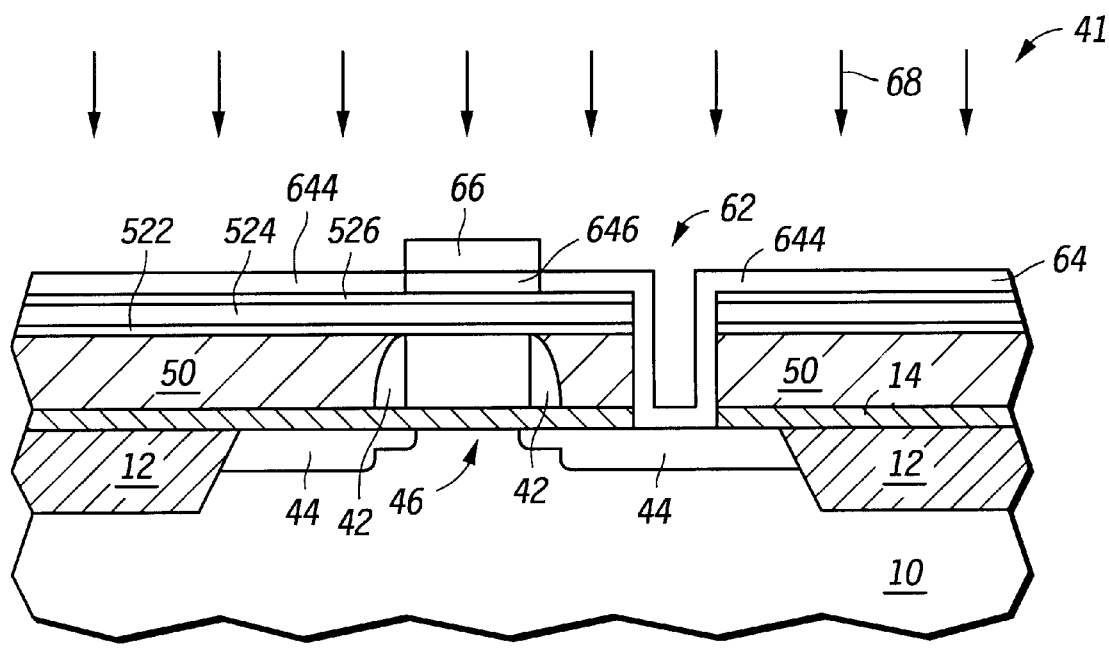
FIG. 6 is a processing step subsequent to FIG. 5.

Generally speaking, the present invention contemplates the use of a metal-organic precursor suitable for forming a high K dielectric layer (i.e., a dielectric layer with a dielectric constant greater than approximately 8) that includes a nitrogen component where the precursor preferably includes a metal-oxygen-nitrogen moiety. The use of a precursor containing such a moiety beneficially enables the use of a single precursor for depositing the dielectric layer thereby simplifying process control parameters and potentially enabling a lower temperature or lower power deposition process.

Turning now to FIG. 1, a dielectric layer 14 is formed over a semiconductor substrate 10 of a semiconductor wafer 11. Semiconductor substrate 10 typically comprises single crystal silicon or other semiconductor material. In the depicted embodiment, isolation dielectric structures 12 have been formed in semiconductor substrate 10 according to isolation techniques well known in the field of semiconductor processing.

Dielectric layer 14 typically has a dielectric constant (permitivity) that is greater than the permitivity of silicon dioxide and is more typically in excess of approximately 8.0. In one embodiment, dielectric layer 14 includes a first element and a second element that is different from the first element where the first element is a metal and the second element is oxygen. In addition, one embodiment of dielectric layer 14 includes a third element different from the first and second element where the third element is nitrogen. In one embodiment, the metal component of the dielectric layer 14 is a Group III, IV, or V transition metal (of the periodic table of elements) such as yttrium (Y), lanthanum (La), titanium (Ti), zirconium (Zr), hafnium (Hf), niobium (Nb), and tantalum (Ta) or other suitable metal such as aluminum (Al).

In one embodiment, dielectric layer 14 is deposited with a chemical vapor deposition process using a precursor according to the present invention that includes a metal-oxygen-nitrogen moiety. In this embodiment, the invention contemplates a method of forming a dielectric layer on a semiconductor substrate by placing the substrate into a CVD reactor chamber and flowing a metal-organic precursor (as described in greater detail below) to form the dielectric layer on the substrate.

Turning now to FIG. 2, in accordance with one embodiment, a chemical compound suitable for use as the precursor for depositing dielectric layer 14 is depicted. In the depicted embodiment, metal-organic precursor 200 includes a metal 202 bonded to an amine 204 by way of oxygen atom 206. Amine 204 includes a nitrogen atom bonded to any alkyl group represented in FIG. 2 by the letter R.

In the depicted embodiment, the metal 202 of precursor 200 is bonded to one or more alkoxy groups 208. In the depicted embodiment, precursor 200 includes a single amine 204 and three alkoxy groups 208 bonded to metal 202. To control the nitrogen content of dielectric layer 14, the number of alkoxy groups 208 may be reduced and the number of amine groups 204 increased. In other words, precursor 200 according to the present invention may include Y amine groups 204 bonded to metal element 202 and (X–Y) alkoxy groups 208 where Y is an integer from 1 to X, and X is an integer from 3 to 5 depending the valency of the metal selected. For zirconium, as an example, which has a valency of 4, X is 4 whereas for aluminum or lanthanum, which have a valency of 3, X is 3). Thus, in accordance with one embodiment, precursor 200 is characterized as an $M(OCR_3)_{X-Y}(ONR_2)_Y$ compound where Y is an integer from 1 to X and X is an integer from 3 to 5 depending upon the valency of the metal M.

Typically, metal 202 is a Group III, IV, or V transition metal such as yttrium, lanthanum, titanium, zirconium, hafnium, niobium, or tantalum or another metal such as aluminum. Thus, precursor 200 includes a metal-oxygen-nitrogen moiety 210, wherein the oxygen is chemically bonded to the metal and to the nitrogen, that facilitates the formation of a nitrogen bearing metal oxide. Because moiety 210 includes a metal-oxygen-nitrogen bond, the use of precursor 200 simplifies the formation of dielectric layer 14 containing a metal-oxygen-nitrogen bond.

Turning now to FIG. 3, an alternative embodiment of precursor 200 is depicted in which one or more of the alkoxy groups of FIG. 2 are replaced with an alkyl siloxy group or siloxy group 212. In this embodiment, precursor 200 is suitable for forming a metal silicate dielectric layer 14 that includes nitrogen (where a metal silicate is a compound having a $M_xSi_yO_z$ structure). Although the embodiment of precursor 200 depicted in FIG. 3 includes a single amine group 204 and three siloxy or alkyl siloxy groups 212, one or more of the siloxy or alkyl siloxy groups may be replaced with amine groups or alkoxy groups (shown in FIG. 2) to control the relative silicon and nitrogen content of dielectric layer 14. Thus, in accordance with an alternative embodiment, precursor 200 can be more generally characterized as a $M(OCR_3)_{X-Y-Z}(ONR_2)_Y(OSiR_3)_Z$ molecule where Y is an integer from 1 to (X−1), Z is an integer from 0 to X−1, X is an integer from 3 to 5 depending upon the valency of M and (Y+Z) is less than or equal to X. While the nitrogen bearing metal silicate formed using the embodiment of precursor 200 depicted in FIG. 3 may result in a dielectric layer 14 with a dielectric constant that is lower than the dielectric constant of the embodiment of precursor 200 described with respect to FIG. 2, it is theorized that the use of a metal silicate may result in an amorphous film. It is further theorized that an amorphous dielectric layer is preferable to a polycrystalline dielectric structure because the grain boundaries inherent in a polycrystalline film may result in increased trap sites or other imperfections undesirable in the dielectric layer 14.

FIG. 4 illustrates a cross-sectional view of a semiconductor device 41 implemented according to one embodiment of the invention. Semiconductor device 41 includes a transistor 400 formed on semiconductor wafer 11 of FIG. 1. Transistor 400 includes a gate electrode (conductor) 40 overlying dielectric layer 14. Thus, in this embodiment, dielectric layer 14 comprises a gate dielectric layer. In other embodiments, dielectric layer 14 may be implemented as a capacitor dielectric structure. Adjacent to gate electrode 40, are two gate spacers 42. Within semiconductor region 10, there are two (a first and a second) doped regions 44. Doped regions 44 may be a source region, a drain region, or a source and drain region. Underlying gate electrode 40 and dielectric layer 14, is a channel region 46 between first and second doped regions 44.

The described variations and different embodiments of dielectric layer 14 of FIG. 1 are applicable to semiconductor device 41. The thickness of dielectric layer 14 is typically less than approximately 10 nm. As described in FIG. 1, dielectric layer 14 includes one or more of a first metal atom, a nitrogen atom, and an oxygen atom where the first metal is a Group III, IV, or V transition metal or another metal such as aluminum. In another embodiment, dielectric layer 14 comprises a metal-silicon oxy-nitride layer that includes at least one silicon atom. The atomic ratio of the nitrogen and oxygen atoms may also vary to form a multi-layered dielectric layer 14. For example, dielectric layer 14 in one embodiment comprises three portions, namely, a first portion adjacent the channel region 46, a third portion adjacent the gate 40, and a second portion that lies between the first portion and the third portion. The second portion may have a substantially lower atomic silicon content than the first and third portions.

Gate electrode 40 typically includes a conductive material, such as a metal, or a semiconductor material, such as polysilicon. In one embodiment, gate electrode 40 includes more than one layer. For example, gate electrode 40 may include a first layer and second layer, wherein the first layer includes a first conductive or semiconductor material and the second layer includes a second conductive or semiconductor material. In one embodiment, the first conductive or semiconductor material and the second conductive or semiconductor material are different types of conductive or semiconductor materials. The width of gate electrode 40 may vary depending on the device specifications and requirements. For this particular embodiment, the width of the gate electrode 40 is typically less than approximately 95 nm.

FIG. 5 illustrates a cross-sectional view of semiconductor device 41 as depicted in FIG. 4 following additional processing and includes an alternative embodiment of the present invention. As depicted in FIG. 5, semiconductor device 41 further includes an insulating layer 50 and a second gate dielectric layer 52. Insulating layer 50 is deposited over gate electrode 40, gate spacers 42, and dielectric layer 14. Following deposition, insulating layer 50 is then typically polished and planarized, stopping at a level substantially equivalent with the top of the gate electrode 40. The second dielectric layer 52, is then deposited over the insulating layer 50. Second dielectric layer 52 may encompass any of the variations and different embodiments described for dielectric layer 14 of FIG. 1 and FIG. 4. In one embodiment, second dielectric layer 52 includes a first silicate layer 522 (i.e., a $M_xO_ySi_z$ layer, where M is a metal), a nonsilicate layer 524 (i.e., an $M_xO_y$), and a second silicate layer 526.

FIG. 6 illustrates a partial cross-sectional view of the semiconductor device 41 of FIG. 5 following further processing that includes an over-gated/under-gated transistor structure as know to one of ordinary skill in the art. As depicted in FIG. 6 semiconductor device 41 further includes a contact opening 62 and a thin layer of conductive material 64. An implant mask 66 is formed over a portion of the conductive material 64. Implant mask 66 is of a material, such as a photoresist, capable of blocking reactive species. The contact opening 62 is created by etching through second dielectric layer 52, insulating layer 50, and first dielectric layer 14. After creating contact opening 62, a conductive material 64 is blanket deposited on semiconductor wafer 10. In one embodiment, the conducting material 64 includes a Group IV element such as titanium, zirconium, or hafnium. Implant mask 66 is placed onto conducting material 64 and positioned substantially above conductive gate 40. In one embodiment, implant mask 66 may be patterned slightly wider that the underlying conductive gate 40 to prevent a subsequent implant from inadvertently doping conductive gate 40. An implant 68 forms doped regions 644 in conducting material 64 on either side of implant mask 66. A channel region 646 underlying implant mask 66 is thereby formed between the doped regions 644.

Figure 7:
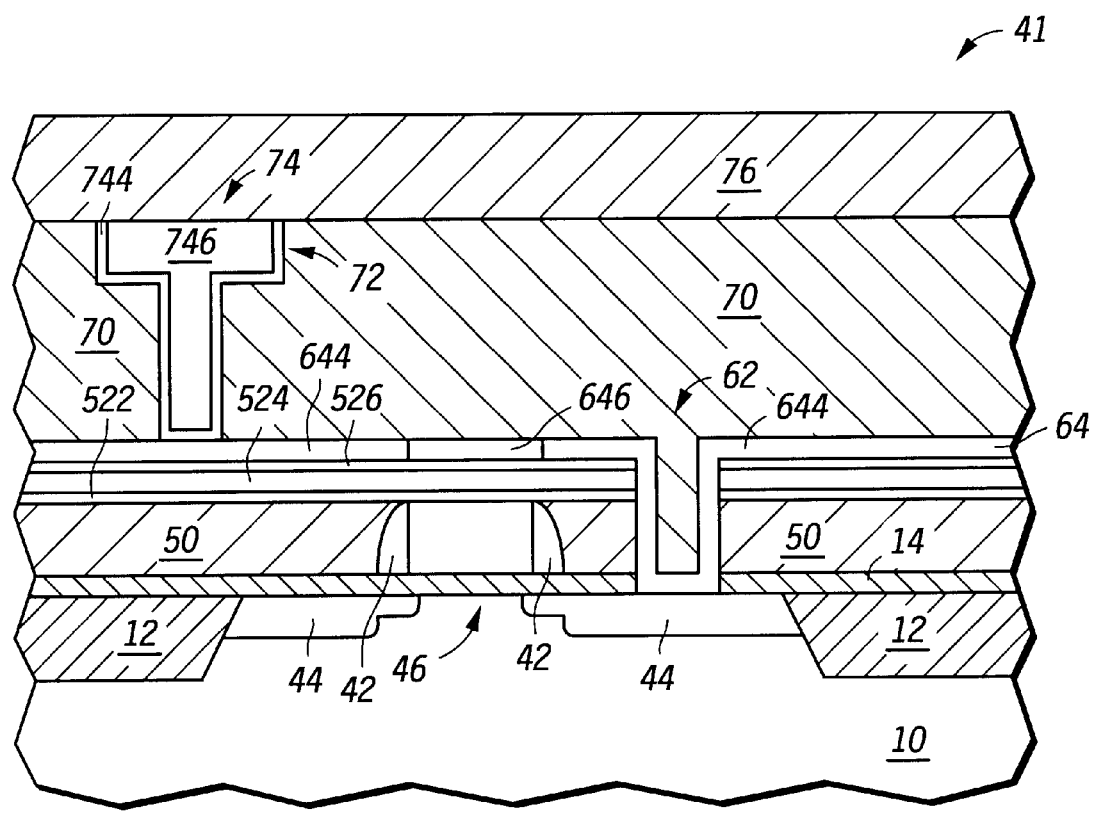
FIG. 7 is a processing step subsequent to FIG. 6 illustrating a semiconductor device according to one embodiment of the invention.

FIG. 7 illustrates a partial cross-sectional view of the semiconductor device 41 shown in FIG. 6 following further processing in accordance with one embodiment. As depicted in FIG. 7, semiconductor device 41 further includes an interlevel dielectric layer 70, a conductive structure 74, and a passivation layer 76. After creating doped regions 644 and channel region 646, an interlevel dielectric layer 70 is blanket deposited upon semiconductor wafer 10. A dual inlaid opening 72 is formed by etching a portion of interlevel dielectric layer 70. A thin barrier layer 744 is deposited within dual inlaid opening 72, which is then filled with a conductive material 746 creating the conductive structure 74. An example of conductive material 746 is copper. In this case, the copper material is then polished back to the surface of interlevel dielectric layer 70. A passivation layer 76 is then deposited onto interlevel dielectric layer 70.

When a bias is applied to conductive gate 40, a conductive path is formed between source/drain regions 44 and between doped regions 644 of conducting material 64 thereby resulting in a conductive path between source/drain region 44 and dual inlaid structure 74. In this manner, a transistor structure are formed both above and below conductive gate 40.

The metal oxy-nitride or a metal-silicon oxy-nitride gate dielectric layer as described in the various embodiments according to the invention can benefit for a number of reasons. For example, the process of forming the gate dielectric layer provides reduced leakage properties and improved thermal stability in the metal oxy-nitride or metal-silicon oxy-nitride film. Further, the dielectric constant is increased allowing more flexibility for scaling the thickness of the dielectric layer. Due to the controllability of the atomic nitrogen concentration, impurity doped diffusion such as boron, phosphorous, and arsenic diffusion through the dielectric layer to the channel is reduced. The control over the interfacial regions between the gate dielectric layer and the gate electrode is improved. The controllability of the nitrogen-to-oxygen atomic gas ratio also results in reduced capacitance versus voltage (CV) hysteresis offset. In addition, embodiments of the present invention can be used to minimize the number of CVD precursors required to deposit the disclosed high K gate dielectric films, which advantageously improves process control requirements by minimizing the number of CVD precursors as well as potentially reduces the deposition power and temperature requirements necessary to achieve the reactivity required by the precursors to form the film.

In the foregoing specification, the invention has been described with reference to specific embodiments. However, one of ordinary skill in the art appreciates that various modifications and changes can be made without departing from the scope of the present invention as set forth in the claims below. Accordingly, the specification and FIGs are to be regarded in an illustrative rather than a restrictive sense, and all such modifications are intended to be included within the scope of the present invention.

Benefits, other advantages, and solutions to problems have been described above with regard to specific embodiments. However, the benefits, advantages, solutions to problems, and any element(s) that may cause any benefit, advantage, or solution to occur or become more pronounced are not to be construed as a critical, required, or essential feature or element of any or all the claims. As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

What is claimed is:

1. A method for forming a dielectric layer on a semiconductor substrate comprising:

placing the semiconductor substrate into a chemical vapor deposition chamber;

flowing a metal-organic precursor into the chemical vapor deposition chamber, wherein the metal-organic precursor includes a moiety having a first metal atom, an oxygen atom, and a nitrogen atom said metal-organic precursor is characterized as an $M(OCR_3)_{x-y-z}(ONR_2)_y(OSiR_3)_z$ molecule wherein M includes a metal atom selected from a group consisting of aluminum, yttrium, lanthanum, titanium, zirconium, hafnium, niobium, and tantalum and where x is an integer from 3 to 5, y is an integer between 1 and x−1, z is an integer from 0 to x−1 and (y+z) is less than or equal to x, wherein the oxygen is chemically bonded to the first metal atom and the nitrogen atom; and forming the dielectric layer on the semiconductor substrate.

2. The method of claim 1, wherein the first metal atom is selected from a group consisting of Group III, Group IV, and Group V transition metals.

3. The method of claim 1, wherein the metal-organic precursor further includes alkoxy groups chemically bonded to the first metal atom.

4. The method of claim 1, wherein the metal-organic precursor further includes alkylsiloxy groups chemically bonded to the first metal atom.

5. The method of claim 1, wherein the metal-organic precursor further includes siloxy groups chemically bonded to the first metal atom.

* * * * *